US00PP11478P

United States Patent [19]

Rijn

[11] Patent Number: Plant 11,478

[45] Date of Patent: Aug. 8, 2000

[54] ANTHURIUM PLANT NAME 'JENNYRIJN'

[75] Inventor: Leonardus van Rijn, Schipluiden, Netherlands

[73] Assignee: Rijnplant B.V., Schipluiden, Netherlands

[21] Appl. No.: 09/177,283

[22] Filed: Oct. 22, 1998

[51] Int. Cl.[7] ..... A01H 5/00

[52] U.S. Cl. ..... Plt./365

[58] Field of Search ..... Plt./365, 367, 368, Plt./369

[56] References Cited

PUBLICATIONS

GTITM UPOVROM Citation for 'Jenny' as Per DE PBR ANT 00028; May 12, 1986.

*Primary Examiner*—Howard J. Locker
*Assistant Examiner*—Kent L. Bell
*Attorney, Agent, or Firm*—C. A. Whealy

[57] ABSTRACT

A distinct cultivar of Anthurium plant named 'Jennyrijn', characterized by its upright, outwardly arching and very freely clumping growth habit; durable, glossy, dark green leaves that are ovate in shape; numerous inflorescences that are positioned upright and above the foliage on strong and erect scapes; durable, glossy dark pink spathes; year-round continuous flowering; and good post-production longevity.

2 Drawing Sheets

BACKGROUND OF THE INVENTION

The present invention relates to a new and distinct cultivar of Anthurium plant, botanically known as *Anthurium andraeanum*, and herinafter referred to by the cultivar name 'Jennyrijn'.

The new Anthurium is a product of a planned breeding program conducted by the Inventor in Schipluiden, The Netherlands. The objective of the program is to create new Anthurium cultivars that have a freely clumping growth habit, strong plant growth, attractive spathe color, numerous inflorescences and leaves, and good post-production longevity.

The new Anthurium originated from a cross by the Inventor on Jul. 20, 1990 of the Inventor's proprietary *Anthurium andraeanum* selection code number 90-6 as the female, or seed, parent with the Inventor's proprietary *Anthurium andraeanum* selection code number 90-5 as the male, or pollen, parent. The cultivar 'Jennyrijn ' was discovered and selected by the Inventor as a plant within the progeny of the stated cross in a controlled environment in Schipluiden, The Netherlands in September, 1993.

Asexual propagation of the new cultivar by tissue culture in a laboratory in Belgium has shown that the unique features of this new Anthurium plant are stable and reproduced true to type in successive generations of asexual propagation.

BRIEF SUMMARY OF THE INVENTION

The new Anthurium has not been observed under all possible environmental conditions. The phenotype may vary somewhat with variations in environment such as temperature and light intensity, without, however, any variance in genotype.

The following traits have been repeatedly observed and are determined to be the unique characteristics of the cultivar 'Jennyrijn'. These characteristics in combination distinguish 'Jennyrijn' as a new and distinct cultivar:

1. Upright, outwardly arching and very freely clumping growth habit.

2. Durable, glossy, dark green leaves that are ovate in shape.

3. Numerous inflorescences that are positioned upright and above the foliage on strong and erect scapes.

4. Durable, glossy dark pink spathes.

5. Year-round continuous flowering.

6. Good post-production longevity.

The new Anthurium can be compared to the female parent, the Inventor's proprietary selection code number 90-6. In side-by-side comparisons conducted by the Inventor in Schipluiden, The Netherlands, plants of the new Anthurium differ from plants of selection code number 90-6 in the following characteristics:

1. Plants of the new Anthurium are more compact than plants of the selection code number 90-6.

2. Plants of the new Anthurium have more durable and thicker leaves that plants of the selection code number 90-6.

3. Plants of the new Anthurium have smaller, thicker and more durable spathes than plants of the selection code number 90-6.

The new Anthurium can be compared to the male parent, the Inventor's proprietary selection code number 90-5. In side-by-side comparisons conducted by the Inventor in Schipluiden, The Netherlands, plants of the new Anthurium differ from plants of selection code number 90-5 in the following characteristics:

1. Plants of the new Anthurium have darker pink spathes than plants of the selection code number 90-5.

2. Plants of the new Anthurium have smaller and more durable leaves that plants of the selection code number 90-5.

3. Plants of the new Anthurium have larger spathes than plants of the selection code number 90-5.

The new Anthurium can be compared to the nonpatented Anthurium cultivar 'Lisette'. In side-by-side comparisons conducted by the Inventor in Schipluiden, The Netherlands, plants of the new Anthurium differ from plants of the cultivar 'Lisette' in the following characteristics:

1. Plants of the new Anthurium have more inflorescences than plants of the cultivar 'Lisette'.

2. Plants of the new Anthurium are more freely clumping than plants of the cultivar 'Lisette'.

3. Plants of the new Anthurium have thicker and more rounded leaves than plants of the cultivar 'Lisette'.

4. Plants of the new Anthurium have thicker and rougher spathes than plants of the cultivar 'Lisette'.

BRIEF DESCRIPTION OF THE PHOTOGRAPHS

The accompanying colored photographs illustrate the overall appearance of the new Anthurium, showing the colors as true as it is reasonably possible to obtain in colored reproductions of this type.

The photograph on the first sheet comprises a top perspective view of a typical potted plant of the cultivar 'Jennyrijn'.

The photograph on the second sheet comprises a close-up view of a typical spathe and spadix of the cultivar 'Jennyrijn'. Leaf, spathe and spadix colors in the photographs may appear different from the actual colors due to light reflectance.

DETAILED BOTANICAL DESCRIPTION

In the following description, color references are made to The Royal Horticultural Society Colour Chart except where general terms of ordinary dictionary significance are used. The following observations and measurements describe one-year old plants grown in Schipluiden, The Netherlands, in a glass greenhouse with an average day temperature of 25° C. and an average night temperature of 19° C.

Botanical classification: *Anthurium andraeanum* cultivar 'Jennyrijn'.

Parentage:

*Female parent.*—Inventor's proprietary *Anthurium andraeanum* selection code number 90-6.

*Male parent.*—Inventor's proprietary *Anthurium andraeanum* selection code number 90-5.

Propagation:

*Method.*—Typically by tissue culture.

*Time to initiate roots.*—About 70 or 84 days at 24° C. or 21° C., respectively.

*Rooting habit.*—Numerous and very strong fleshy roots.

Plant description:

*Plant shape.*—Upright, inverted triangle, symmetrical.

*Growth habit.*—Erect when young, becoming outwardly arching as leaves develop. Freely clumping, bushy and dense. Appropriate for 17 to 35-cm containers.

*Plant height.*—About 50 cm from soil level to apex of spathes.

*Plant vigor.*—High.

*Growth rate.*—Moderate to rapid.

*Crop time.*—About 10 months are usually required from planting of young plants to finished plants in 17-cm containers.

*Foliage description.*—Quantity: Usually about 30 leaves per container. Length: About 22.5 cm. Width: About 16 cm. Shape: Ovate. Apex: Apiculate. Base: Auriculate to cordate; lobes not overlapping. Margin: Entire, slightly undulating. Texture: Smooth, glabrous, leathery. Color: Young leaves, upper surface: Brownish red to green. Young leaves, lower surface: Brownish red to green. Mature leaves, upper surface: Darker than 139A, glossy. Mature leaves, lower surface: Darker than 144A. Petiole: Length: About 33 cm. Color: 144A to 146C with slight anthocyanin. Geniculum length: About 3 cm.

Inflorescence description:

*Inflorescence arrangement.*—Spathe with spadix held above the foliage. Flowering structures arise from leaf axils. Freely flowering; continuous flowering year-round; typically four to seven inflorescences per plant. Not fragrant.

*Inflorescence longevity.*—Inflorescences last about six weeks under winter conditions and up to three months under summer conditions; persistent.

*Flowers.*—Quantity per spadix: Numerous, about 150 to 200. Shape: Rounded. Diameter: About 1 mm, maximum.

*Spathe.*—Length: About 6cm. Width: About 5.25 cm. Height above foliage: About 2 cm. Shape: Deltoid. Apex: Mucronate. Base: Auriculate to cordate; lobes not overlapping. Margin: Entire. Texture: Leathery, glabrous, some blistering, glossy. Color: When opening: 39B. Front surface: 50A to 52A. Back surface: 52C to 52D. After senescence: 51A to 54A.

*Spadix.*—Length: About 4.5 cm. Diameter: About 8 mm. Shape: Columnar. Cross section: Rounded. Longitudinal axis: Straight, erect. Color: Base: Creamy white with slight pink coloration. Mid-section: 33B to 51C. Apex: 33B. Color, after senescence: 151C to 144C, base creamy white; apex, 51C.

*Scape.*—Length: About 35 cm. Aspect: Strong and erect. Color: 144A with anthocyanin towards apex.

*Reproductive organs.*—Androecium: Pollen color: Creamy white. Gynoecium: Stigma shape: Ovoid.

Disease resistance: Plants of the new Anthurium have not been shown to be resistant to diseases common to Anthurium.

Seed development: Seed development on plants of the new Anthurium has not been observed.

It is claimed:

1. A new and distinct cultivar of Anthurium plant named 'Jennyrijn', as illustrated and described.

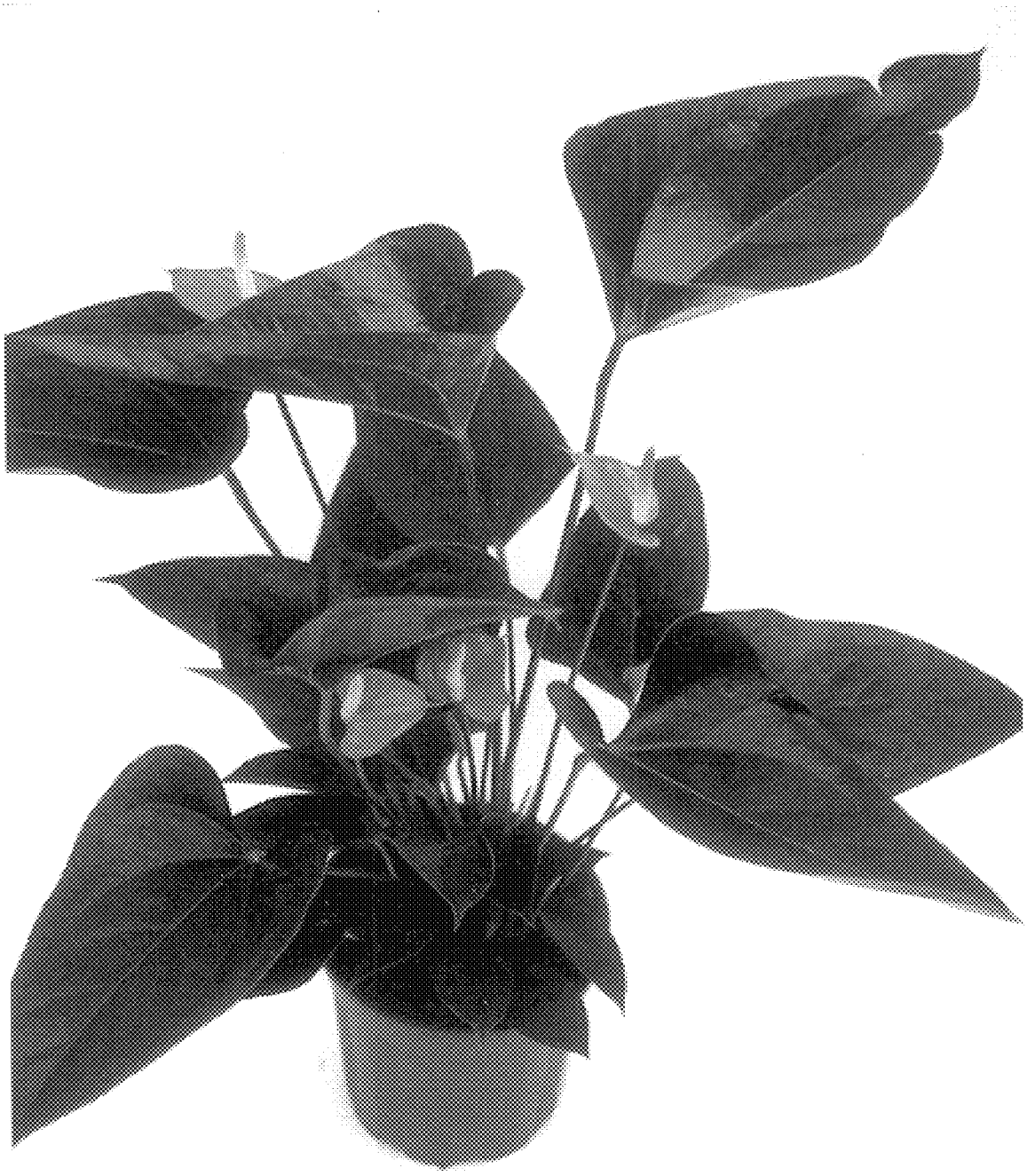

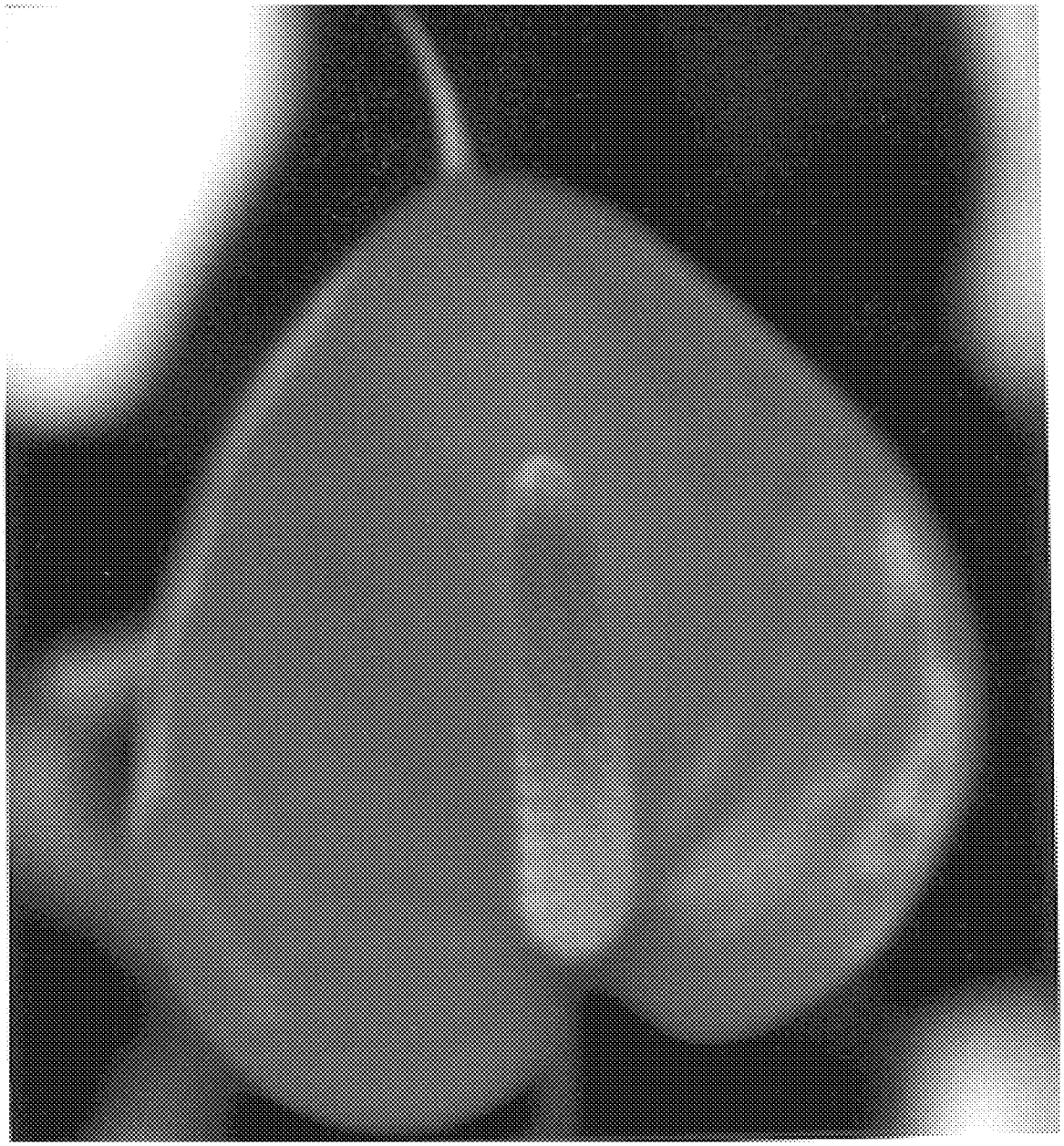

* * * * *